(12) United States Patent
Lee et al.

(10) Patent No.: US 6,818,625 B2
(45) Date of Patent: Nov. 16, 2004

(54) METHOD FOR INCREASING SURVIVAL RATE OF CELLS IN ANIMAL CELL CULTURE UNDER HYPOXIA CONDITION

(75) Inventors: Jongwon Lee, Taegu (KR); Kyu-Won Kim, Pusan (KR); Mee-Jung Han, Taejon (KR); Moo Hwan Cho, Taegu (KR); Yang-Il Kim, Taegu (KR)

(73) Assignee: Hypoxi Co., Ltd. (KR)

( * ) Notice: Subject to any disclaimer, the term of this patent is extended or adjusted under 35 U.S.C. 154(b) by 0 days.

(21) Appl. No.: 10/181,221

(22) PCT Filed: Jan. 12, 2001

(86) PCT No.: PCT/KR01/00051

§ 371 (c)(1),
(2), (4) Date: Jul. 12, 2002

(87) PCT Pub. No.: WO01/51615

PCT Pub. Date: Jul. 19, 2001

(65) Prior Publication Data

US 2003/0022366 A1 Jan. 30, 2003

(30) Foreign Application Priority Data

Jan. 12, 2000  (KR) .......................................... 2000-1309

(51) Int. Cl.⁷ ........................ A61K 31/70; A61K 31/65; A61K 31/497
(52) U.S. Cl. ........................... 514/35; 514/36; 514/37; 514/38; 514/39; 514/40; 514/152; 514/254
(58) Field of Search .............................. 514/35, 36, 37, 514/38, 39, 40, 152, 254, 311, 33, 34, 41

(56) References Cited

U.S. PATENT DOCUMENTS 5,677,288 A * 10/1997 Marangos .................... 514/39

OTHER PUBLICATIONS

Madigan, M. T., et al. (1997) Brock Biology of Microorganisms: Eighth Edition, p. 414–418, Prentice Hall International, Inc.

Wilhelm, J. M., et al. (1978) Aminoglycoside Antibiotics and Eukaryotic Protein Synthesis: Structure–Function Relationships in the Stimulation of Misreading with a Wheat Embryo System. Biochemistry 17(7):1143–1149.

Mingeot–LeClercq, M.–P., et al. (1999) Aminoglycosides: Activity and Resistance. Antimicrob. Agents Chemother. 43(4):727–737.

Takei, M., et al. (1998) Inhibitory Activities of Gatifloxacin (AM–1155), a Newly Developed Flouroquinolone, against Bacterial and Mammalian Type II Topoisomerases. Antimicrob. Agents Chemother. 42(10):2678–2681.

International Search Report dated May 30, 2001 from International Application No. PCT/KR01/00051.

* cited by examiner

*Primary Examiner*—Elli Peselev
(74) *Attorney, Agent, or Firm*—Knobbe, Martens, Olson & Bear, LLP

(57) ABSTRACT

The present invention relates to a method for increasing survival rate of cells in animal cell culture under hypoxia condition by adding antibiotics to the culture media. The method of present invention comprises a step of culturing animal cells in culture media containing antibacterial agent of quinolones, quinones, aminoglycosides or chloramphenicol at the concentration range of 0.1 to 1000 μg/ml. The invented method can be practically applied for high-density animal cell culture to produce recombinant proteins or cultured cells.

6 Claims, 6 Drawing Sheets

METHOD FOR INCREASING SURVIVAL RATE OF CELLS IN ANIMAL CELL CULTURE UNDER HYPOXIA CONDITION

CROSS-REFERENCE TO RELATED APPLICATIONS

This is the U.S. National Phase under 35 U.S.C. § 371 of International Application No. PCT/KR01/00051, filed Jan. 12, 2001 and published in English, which claims priority to Korean Application No. 2000/1309, filed Jan. 12, 2000.

BACKGROUND OF THE INVENTION

1. Field of the Invention

The present invention relates to a method for increasing viability of animal cells in culture under hypoxia condition, more specifically, to a method for increasing survival rate of cells in animal culture under hypoxia condition by adding antibiotics to the culture medium.

2. Description of the Prior Art

Most of animal cells require oxygen as a substrate in addition to nutrients for living. Thus, insufficient supply of oxygen to cells may cause various problems in medicine and industry. For example, in developing artificial organs including artificial liver, if the supply of nutrients and oxygen is hampered by limitation of mass transfer into the cells, the cells become died, especially, in case of using encapsulated cells, oxygen transfer is a more serious problem (see: Catapano et al., Int. J. Artif. Organs, 19(1):61–71, 1996).

In case of myocardial infarction and cerebral infarction, the blockage of blood vessels by which oxygen is supplied to tissues may hinder blood flow, resulting in necrosis of the tissues (see: Selwyn et al., Ischemic heart disease, 1077–1085, In: Isselbacher et al. (eds.), Harrison's Principles of Internal Medicine, 13th ed., McGraw-Hill, Inc., New York). In this case, an inadequate supply of glucose which is used as an energy source by cells as well as an inadequate supply of oxygen make the situation more serious.

Recently, high-density animal cell culture is one of the popular techniques used for production of recombinant proteins or for production of cultured cells. As animal cells do not have cell walls differently from microorganisms, animal cell membranes may be easily destroyed by mechanical agitation or a contact with air, which makes it very difficult to supply oxygen into culture medium by agitation, resulting in reduction of final concentration of the cells.

In order to solve the oxygen transfer problem, attempted are a method for increasing dissolved oxygen concentration by adding purified hemoglobin which can bind to perfluorohydrocarbon or oxygen; a method for increasing yield of energy production using electron acceptors such as is fumaric acid other than oxygen; and, a method for increasing available oxygen inside the cells by expressing genetically manipulated hemoglobin in the cells. Also, recently attempted is a method for increasing resistance of cardiac cells to hypoxic condition by affecting energy metabolism pathway using trimetazidine. The said methods, however, have revealed disadvantages as followings: first, there is a limitation in improving the efficacy by adding perfluorohydrocarbon or hemoglobin to a culture medium since it does not change intrinsic property of cells but simply increases concentration of dissolved oxygen or promotes oxygen transfer; secondly, there is a limitation in an effective concentration range of electron acceptors like fumaric acid since the electron acceptors become reduced; thirdly, the method for increasing oxygen transfer by expressing recombinant genes in the cells requires complicated process and is very costly.

Under the circumstances, there are strong reasons for exploring and developing an alternative method for increasing viability of animal cells in culture under a low oxygen condition.

SUMMARY OF THE INVENTION

The present inventors have made an effort to develop a method for increasing the viability of animal cells in culture under hypoxia condition, and found that the survival rate of animal cells in culture under a low oxygen condition can be dramatically increased by growing cells in a medium containing antibiotics of quinolones, quinones, aminoglycosides or chloramohenicol in a concentration range of 0.1–1000 $\mu$g/ml.

The primary object of the present invention is, therefore, to provide a method for increasing survival rate of cells in animal cell culture under hypoxia condition.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

The method for increasing survival rate of cells in animal cell culture under hypoxia condition comprises the steps of adding antibiotics of quinolones, quinones, aminoglycosides or chloramphenicol in a concentration of 0.1 to 1000 $\mu$g/ml to a culture medium and culturing the animal cells. The antibiotics include quinolones, quinones and aminoglycosides, but are not intended to be limited to, where the quinolone antibiotics include levofloxacin, ofloxacin and ciprofloxacin; quinone antibiotics include tetracycline, minocycline, doxycycline, and oxytetracycline; and, aminoglycoside antibiotics include geneticin, neomycin and gentamycin.

A variety of animal cells are available, which include human hepatoma cell line HepG2(ATCC HB 8065), human liver cell line Chang liver (ATCC CCL 13), murine neuronal cell line C6(ATCC CCL 107), human neuroblastoma cell line BE2 cells (ATCC TIB 182), lymphoma cell line 5F12AD3 (ATCC HB 8209) or bovine aortic endothelial cells (BAE). As the culture medium, it is preferred that a Minimal Essential Medium supplemented with 70–130 unit/ml penicillin, 90–110 $\mu$g/ml streptomycin, 0.8 to 1.5 g/l glucose, 1.5 to 3 g/l sodium bicarbonate, and 8–12% (v/v) fetal calf serum is for HepG2; Dulbecco's Modified Medium supplemented with 8–12% (v/v) inactivated fetal calf serum for BE2; Iscove's Modified Dulbecco's Medium supplemented with 8–12% (v/v) fetal calf serum for 5F12AD3.

The present inventors cultured animal cells under normal condition and observed the changes occurred in the cells after discontinuing the supply of oxygen and glucose, which revealed that the cells were died without utilization of lactic acid together with depletion of glucose when oxygen was depleted in the cells. Further, when oxygen supply was resumed immediately after depletion of glucose, cells could survive as long as lactic acid was used up, but finally cells died with exhaustion of lactic acid.

Analyses of various test groups of cells under a condition of oxygen and glucose depletion have shown that the groups of cells without antibiotic treatment underwent typical apoptosis, whereas, the groups of cells treated with said antibiotics did not undergo apoptosis for a certain period of time. These results imply that the said antibiotics inhibit apoptosis occurred in cells with ischemic injury which lacks an adequate supply of oxygen and glucose. Additional experiments demonstrated that antibiotics somehow affect the expression of bcl-2 protein which is known to be an inhibitor of apoptosis in cells with ischemic injury.

The present invention is further illustrated in the following examples, which should not be taken to limit the scope of the invention.

EXAMPLE 1
Cell Viability under Various Oxygen Conditions

Figure 1:
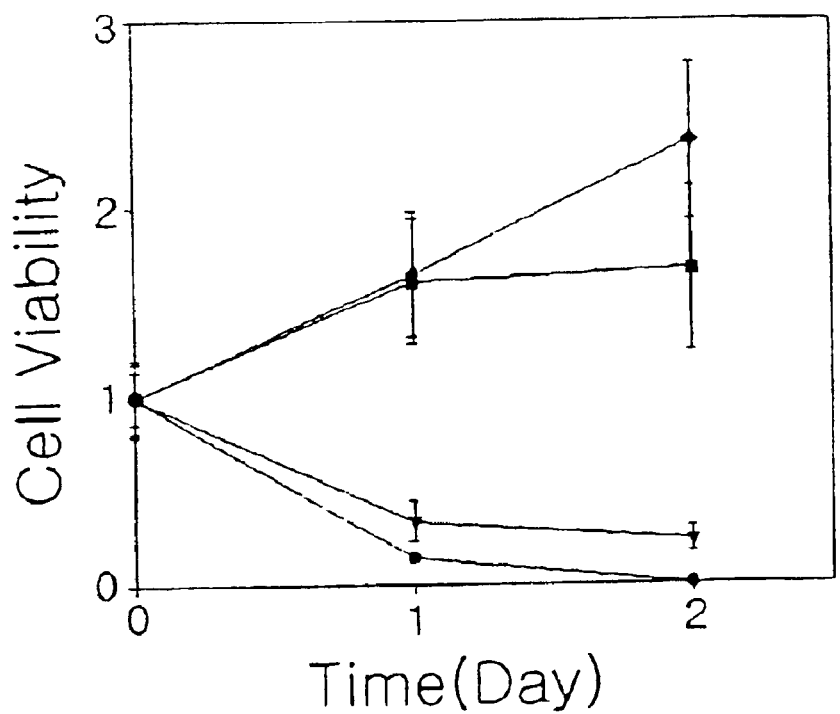
FIG. 1 is a graph showing HepG2 cell viability under various oxygen conditions.

HepG2 cells (human hepatoma cell line, ATCC HB 8065, 1×10$^6$ cells/60 mm culture dish) were grown in a Minimal Essential Medium supplemented with 100 unit/ml penicillin, 100 $\mu$g/ml streptomycin, 1 g/l glucose, 2.2 g/l sodium bicarbonate, and 10% (w/v) fetal calf serum for 2 days, followed by feeding with the same medium and incubating under an environment of 1, 2, or 5% (v/v) oxygen, respectively. Numbers of viable cells with time were determined by trypan blue exclusion assay using hemocytometer after 10–15 minutes of incubation of 1:1 (v/v) mixture of 0.4% (w/v) trypan blue and cell suspension. Cell viability with time was represented in the ratio of viable cell number to cell number just before the incubation condition was changed to a low oxygen condition (see: FIG. 1). FIG. 1 is a graph showing cell viability under various oxygen conditions, where (●) indicates 1% (v/v), (▲) indicates 2% (v/v), (■) indicates 5% (v/v), and (♦) indicates 21% (v/v) oxygen, respectively. As shown in FIG. 1, it was clearly demonstrated that HepG2 cells were viable in a minimal medium containing low concentration of glucose under an environment over 5% (v/v) oxygen, whereas, the cells died under an environment of less than 2% (v/v) oxygen. Accordingly, a low oxygen condition was set at 1% (v/v) oxygen in the following examples.

EXAMPLE 2
Dependency of Cell Viability on Geneicin Concentration

Dependency of cell viability on geneticin concentration was determined under a low glucose (1 g/L) or a high glucose (4.5 g/L) condition, as well as under a low oxygen (1%, v/v) or normal oxygen condition.

Figure 2A:
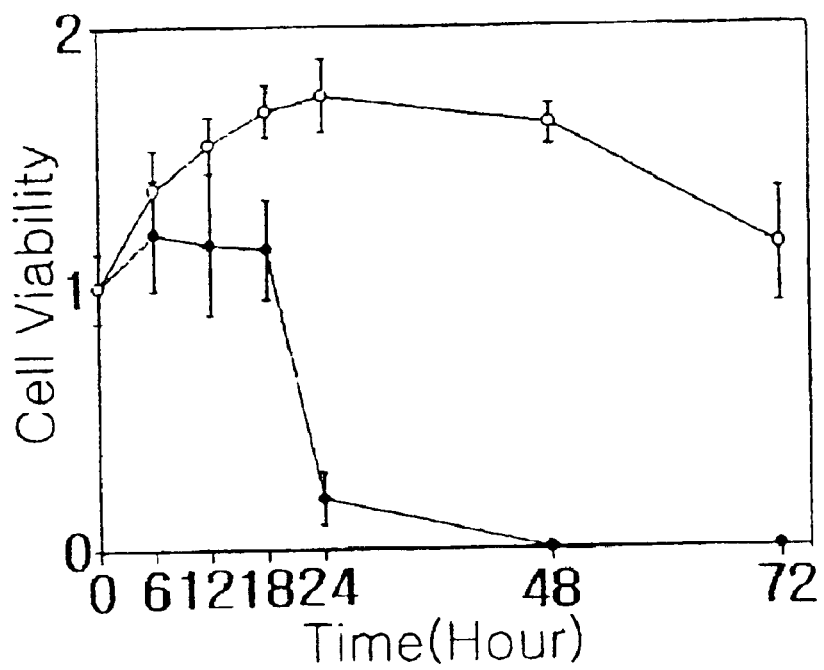
FIG. 2a is a graph showing cell viability of HepG2 with incubation time under a low oxygen and a low glucose condition.
Figure 2B:
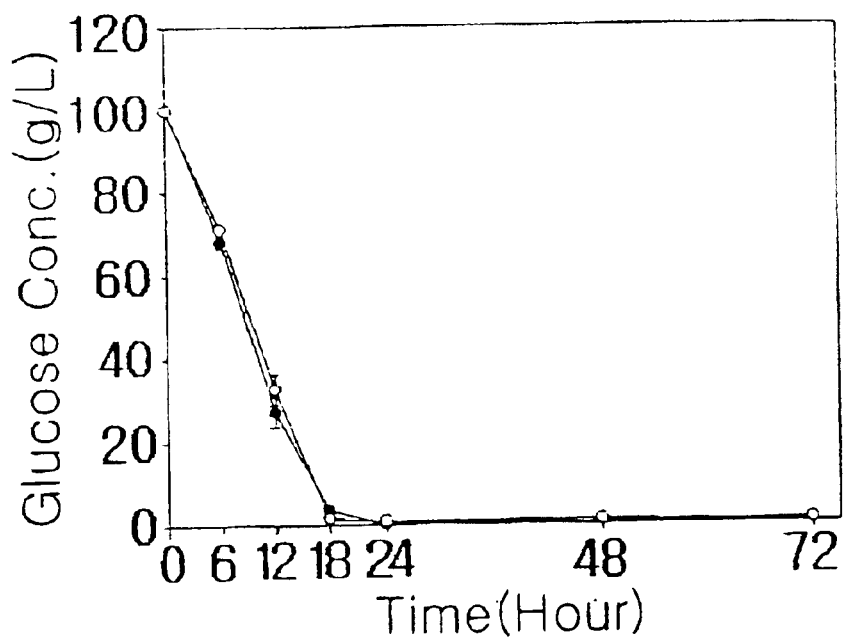
FIG. 2b is a graph showing the change in residual glucose concentration with incubation time under a low oxygen and a low glucose condition.
Figure 2C:
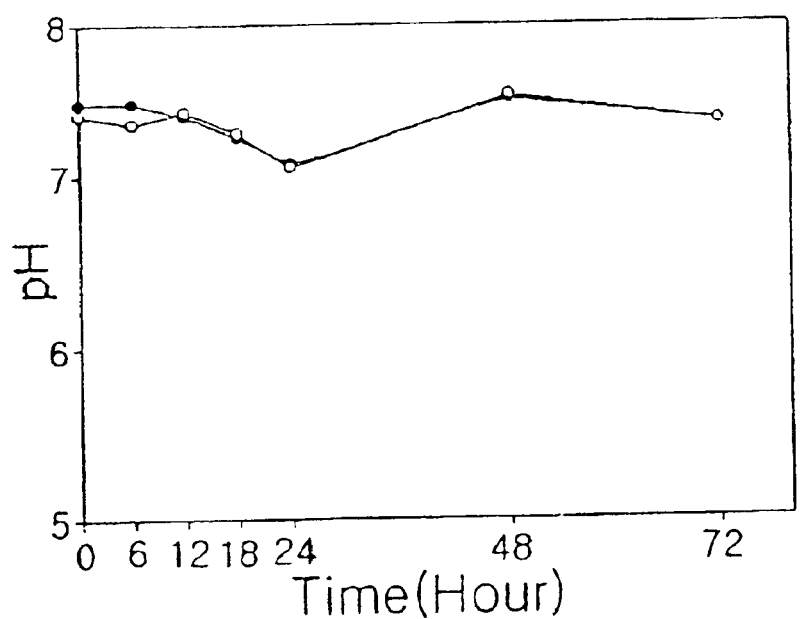
FIG. 2c a graph showing the change in pH with incubation time under a low oxygen and a low glucose condition.

EXAMPLE 2-4
Cell Viability under a Low Oxygen (Hypoxic) and a Low Glucose (Hypoglycemic) Condition HepG2 cells were plated in 60 mm culture dishes at a density of 5×10$^5$ cells per dish under a condition of 1 g/L glucose and 1% (v/v) oxygen, and then, cell viability, changes in pH and changes in glucose concentration were determined with time after adding 10 $\mu$g/ml geneticin or without addition (see: FIGS. 2a, 2b and 2c). FIG. 2a shows HepG2 cell viability with incubation time, 2b shows change in glucose concentration with incubation time, and 2c shows change in pH with incubation time, where (●) indicates without addition and (○) indicates addition of 10 $\mu$g/ml geneticin. As shown in FIGS. 2a to 2c, geneticin maintained cell viability even after glucose was used up under a hypoxic and hypoglycemic condition.

Figure 3A:
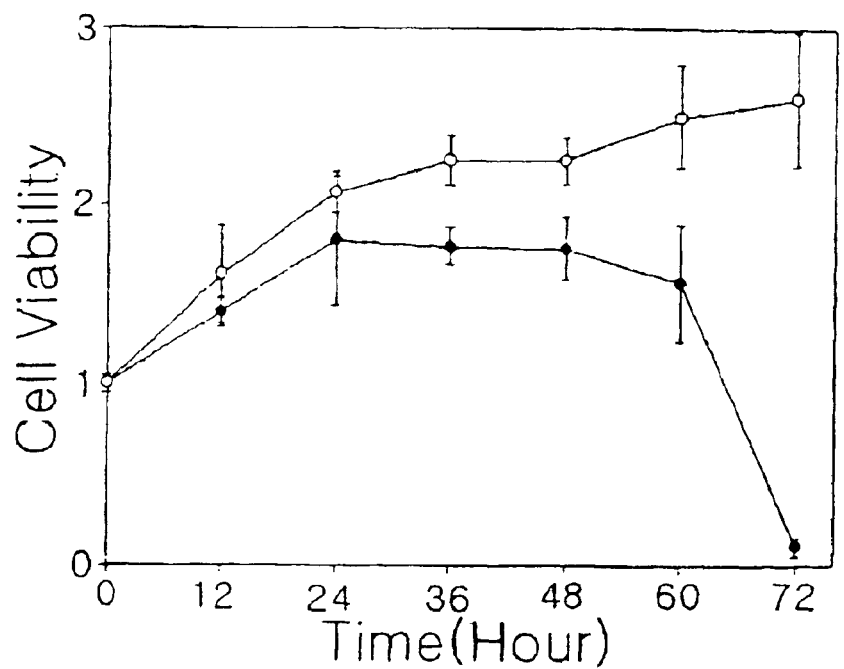
FIG. 3a is a graph snowing cell viability of HepG2 with incubation time under a low oxygen and a high glucose condition.
Figure 3B:
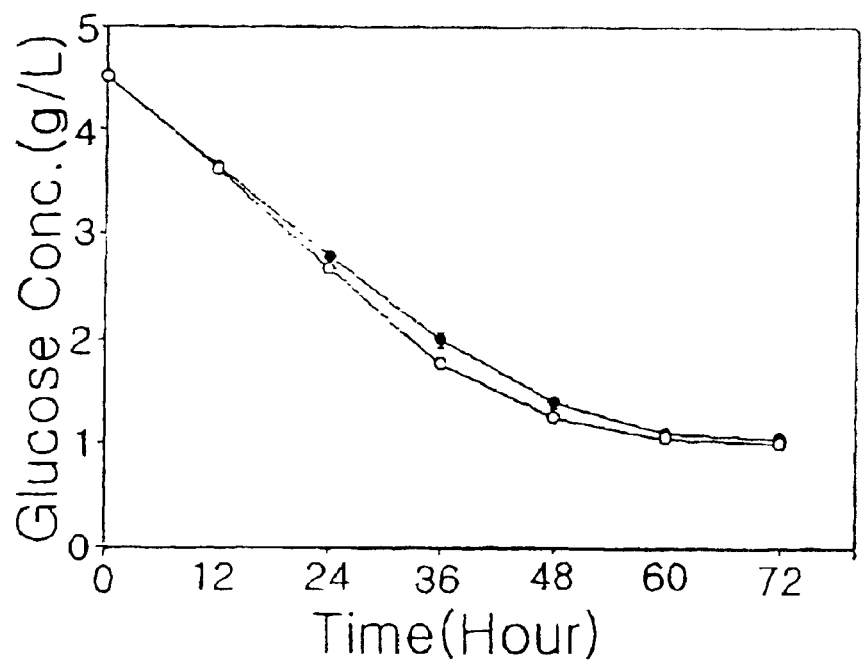
FIG. 3b is a graph showing the change in residual glucose concentration with incubation time under a low oxygen and a low glucose condition.
Figure 3C:
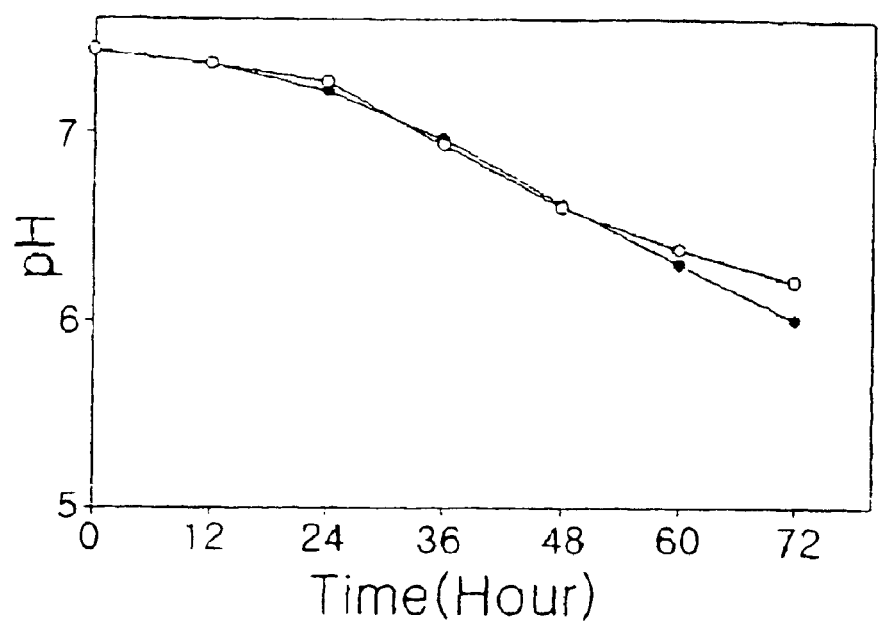
FIG. 3c is a graph showing the change in pH with incubation time under a low oxygen and a low glucose condition.

EXAMPLE 2-2
Cell Viability under a Low Oxygen (Hypoxic) and a High Glucose Condition HepG2 cells were grown under the same condition described in Example 2-1 except 4.5 g/L glucose and 1% (v/v) oxygen, and then, cell viability, changes in pH and changes in glucose concentration were determined with time after treatment with 10 $\mu$/g/ml geneticin or without treatment, respectively (see: FIGS. 3a, 3b and 3c). FIG. 3a shows HepG2 cell viability with incubation time, 3b shows changes in glucose concentration with incubation time, and 3c shows changes in pH with incubation time, where (●) indicates without treatment and (○) indicates treatment with 10 $\mu$g/ml geneticin. As shown in FIGS. 3a to 3c, it was clearly demonstrated that geneticin maintained cell viability under a hypoxic and high glucose condition in a similar manner under a hypoxic and hypoglycemic condition.

Figure 4A:
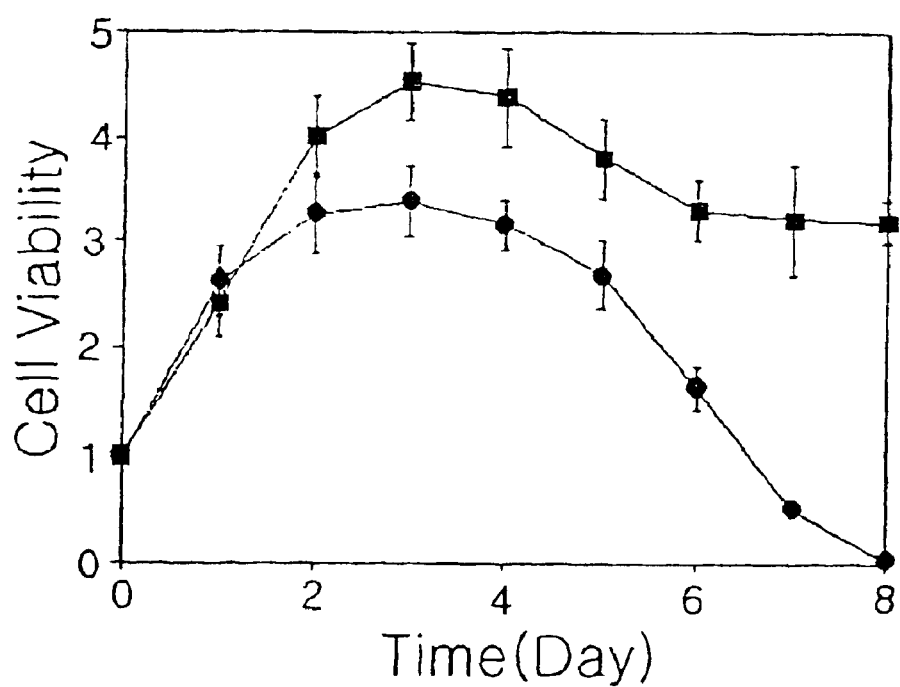
FIG. 4a is a graph showing cell viability of HepG2 with incubation time under a normal oxygen and a low glucose condition.
Figure 4B:
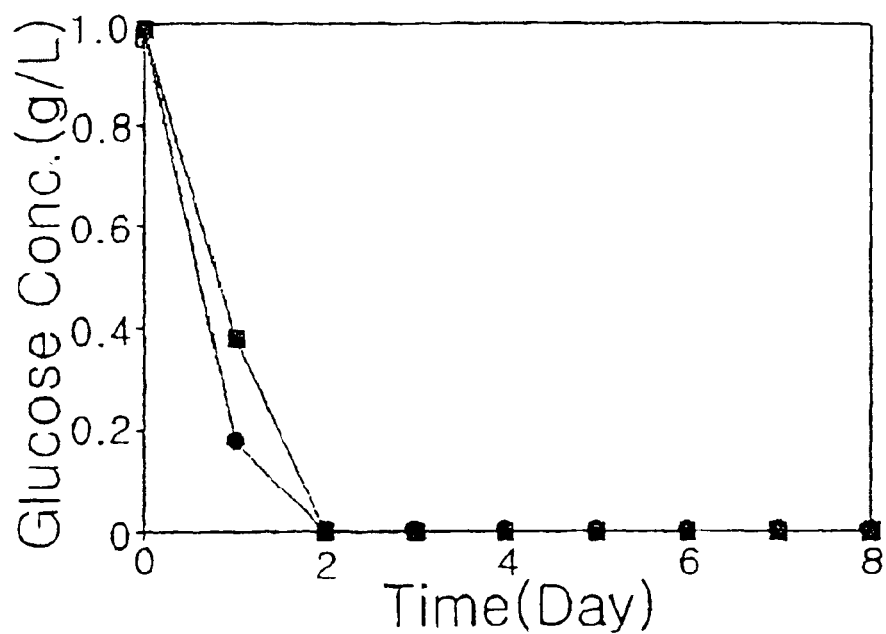
FIG. 4b is a graph showing the change in residual glucose concentration with incubation time under a normal oxygen and a low glucose condition.
Figure 4C:
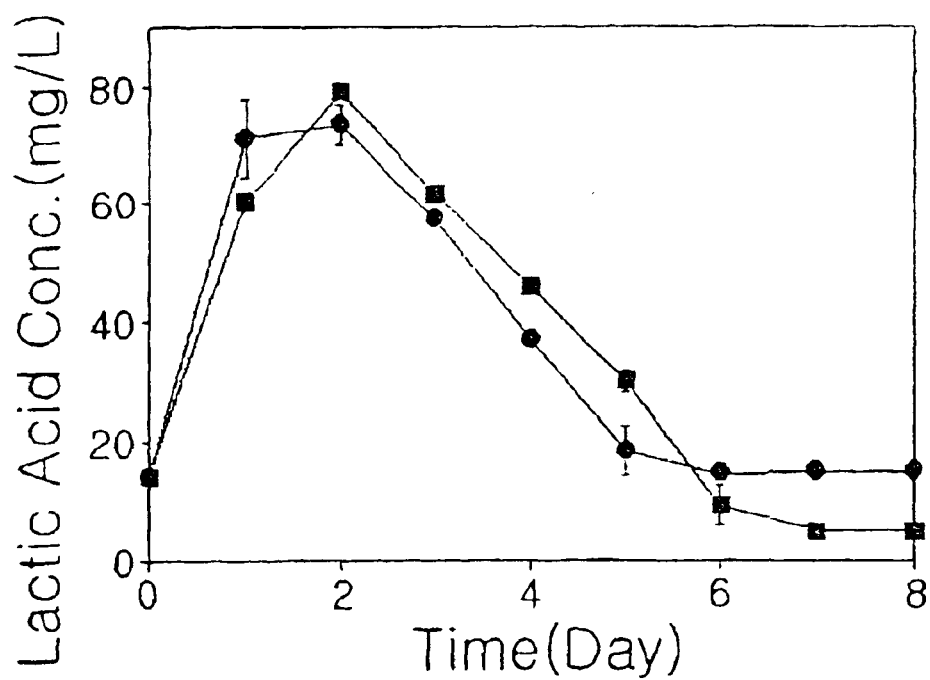
FIG. 4c a graph showing the change in lactic acid concentration with incubation time under a normal oxygen and a low glucose condition.

EXAMPLE 2-3
Cell Viability under a Normal Oxygen (Normoxic) and a Low Glucose (Hypoglycemic) Condition HepG2 cells were grown in the same manner as in Example 2-1 except for 1 g/L glucose and 21% (v/v) oxygen, and then, cell viability, change in glucose concentration and change in lactic acid concentration were determined with time after adding 10 $\mu$g/ml geneticin or without addition (see: FIGS. 4a, 4b and 4c). FIG. 4a shows HepG2 cell viability with incubation time, 4b shows change in glucose concentration with incubation time, and 4c shows change in lactic acid concentration with incubation time, where (●) indicates without treatment and (■) indicates treatment with 10 $\mu$g/ml geneticin. As shown in FIGS. 4a to 4c, under normoxic condition, cells survived while consuming accumulated lactic acid after depletion of glucose and cells died with exhaustion of lactic acid, whereas, cells treated with geneticin were viable without being affected by depletion of lactic acid.

EXAMPLE 3
Effects of Various Antibiotics on Cell Viability

Figure 5:
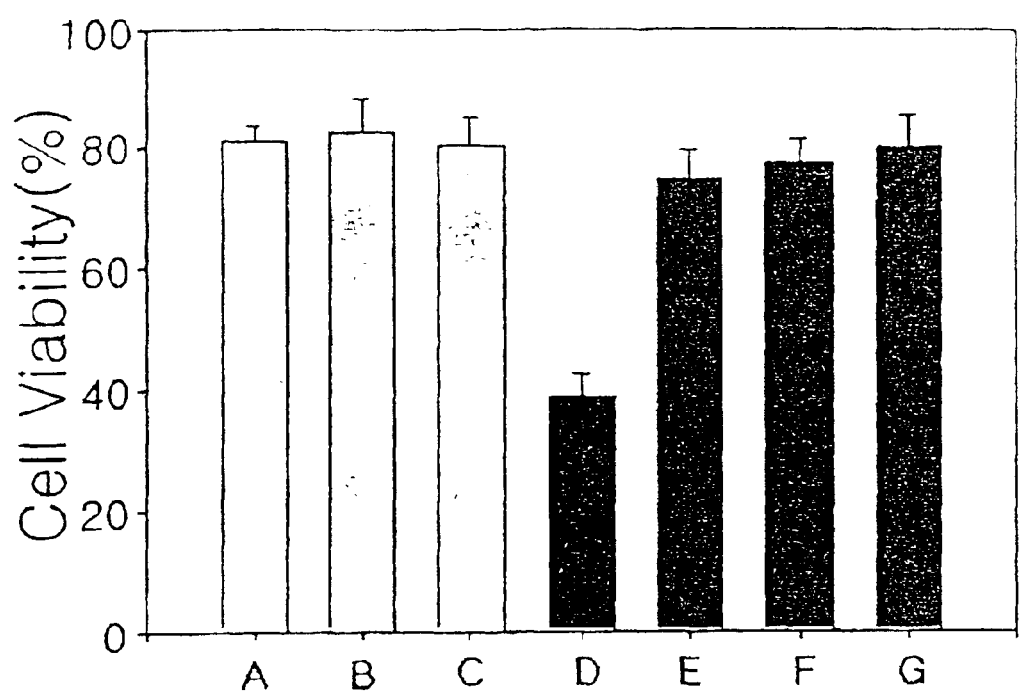
FIG. 5 is a graph showing cell viability of HepG2 treated with various antibiotics.

In order to screen antibiotics which have similar effect to geneticin but have different chemical structure, HepG2 (Human hepatoma cell line, ATCC HB 8065) cells were grown under the same condition described in Example 1, followed by replacing the medium with fresh medium proper for test conditions described below, and then, cell viabilities under various conditions were compared after 2 days of incubation. Test groups were divided as follows depending on test conditions: test group A with 21% (v/v) oxygen and 4.5/L glucose, test group B with 21% (v/v) oxygen and 1 g/L glucose, test group C with 1% (v/v) oxygen and 4.5/L glucose, tesy group D with 1% (v/v) oxygen and 1 g/L glucose, test group E with aminoglycoside antibiotic of geneticin (10 µg/ml) treated test group D, test group F with quinolone antibiotic of ofloxacin (10 µg/ml) treated test group D, and test group G with quinone antibiotic of doxycycline (0.1 µg/ml) treated test group D (see: FIG. 5) FIG. 5 is a graph showing the comparison of effects of various antibiotics on the cell viability. As shown in FIG. 5, it has been found that: cell viability of test group D was low compared to test groups A, B and C, and cell viability of test group D can be recovered by treatment of various antibiotics.

EXAMPLE 4
Screening of Antibiotics Exerting Positive Effects on Cell Viability Based on the results obtained in Example 3 above, it was found that antibiotics of quinolones and quinones as well as aminoglycosides can enhance cell viability under hypoxia condition. In order to examine whether antibiotics with other structures than aminoglycoside antibiotics, can also enhance cell viability under a hypoxic condition, analyses were performed as followings: i.e., after analysis of antibiotics such as geneticin, neomycin, gentamycin, tetracycline, minocycline, oxytetracycline, doxycycline, chloramphenicol, levofloxacin, ofloxacin, cidrofloxacin, ampicillin, amoxicillin, cephalosporin, erythromycin, sulfadiazine, cyclohexamide, 5-fluorouracil, puromycin and trimetazidine in accordance with the procedure described in Examples 2-1 and 2-2, antibiotics which showed enhancement of cell viability under hypoxic condition were selected and their effective concentrations were determined, respectively (see: Table 1).

TABLE 1

Antibiotics exerting enhancement effects on cell viability and their effective concentration

| Antibiotics | Concentration(µg/ml) |
| --- | --- |
| geneticin | 10–100 |
| neomycin | 1000 |
| gentamicin | 100–1000 |
| tetracycline | 0.1–10 |
| minocycline | 0.1–10 |
| doxycycline | 0.1–10 |
| oxytetracycline | 0.1–10 |
| chloramphenicol | 1–10 |
| levofloxacin | 10–100 |
| ofloxacin | 10–100 |
| ciprofloxacin | 1–10 |

Effective concentration ranges in Table 1 represent the concentration ranges of antibiotics exerting enhancement effects on HepG2 cell viability under 1% (v/v) oxygen condition. As shown in Table 1 above, among the antibiotics known to act on 30S subunit of ribosome in E. coli, neomycin and gentamycin other than geneticin were effective among aminoglycoside antibiotics. Also, among the antibiotics known to act on 30S subunit of ribosome in E. coli, a aromatic antibiotic of tetracycline was effective at very low concentration range of 0.1–10 µg/ml, and tetracycline derivatives such as minocycline, oxytetracycline and doxycycline were effective at the same range of low concentration. Meanwhile, among the antibiotics known to act on 50S subunit of ribosome in E. coli, an aromatic antibiotic of chloramphenicol was effective, but a macrolide antibiotic of erythromycin was not effective. Among quinolone antibiotics known to act on DNA gyrase, all analyzed compounds, levofloxacin, ofloxacin, and ciprofloxacin were effective. However, antibiotics known to inhibit synthesis of cell wall of microorganisms, such as ampicillin, amoxillin, and cephalosporin did not show enhancement effect on cell viability. Antibiotics such as a sulfadiazine which is known to inhibit dihydropteroate synthetase in the folic acid metabolism, a cyclohexamide inhibiting protein synthesis in eukaryotes, a 5-fluorouracil blocking DNA synthesis by competing with uracil, and puromycin inhibiting protein synthesis did not show any effect on cell viability. Based on these results, it has been demonstrated that there is no significant relations between the ability of antibiotics to enhance cell viability under hypoxic condition and the action mechanism of antibiotics or the chemical structure of antibiotics. Although efficacy of antibiotics to maintain cell viability under hypoxic condition varies, effective concentration range of antibiotics on enhancement of viability of human hepatoma cell line was about 0.1 to 1000 µg/ml. Meanwhile, trimetazidine which is known to enhance cell viability by increasing utilization of glucose under a hypoxic condition did nor show any positive result in the present invention.

As clearly illustrated and demonstrated above, the invention provides a method for increasing survival rate of cells in animal cell culture under hypoxia condition, which comprises the steps of adding antibiotics of quinolones, quinones, aminoglycosides or chloramphenicol in a concentration of 0.1 to 1000 µg/ml to a culture medium and culturing the animal cells. The invented method can be practically applied to a mass production of recombinant protein and a high-density animal cell culture.

Various modifications of the invention in addition to those shown and described herein will be apparent to those skilled in the art from the foregoing description. Such modifications are also intended to fall within the scope of the appended claims.

What is claimed is:

1. A method for increasing survival rate of cells in animal cell culture under hypoxia condition, which comprises the steps of adding antibiotics of quinolones, quinones, or chloramphenicol in a concentration of 0.1 to 1000 µg/ml to a culture medium and culturing animal cells.

2. The method for increasing survival rate of cells in animal cell culture under hypoxia condition of claim 1, wherein the quinolone antibiotics are selected from the group consisting of levofloxacin, ofloxacin and ciprofloxacin.

3. The method for increasing survival rate of cells in animal cell culture under hypoxia condition of claim 1, wherein the quinone antibiotics are selected from the group consisting of tetracycline, minocycline, doxycycline and oxytetracycline.

4. The method for increasing survival rate of cells in animal cell culture under hypoxia condition of claim 1, wherein the animal cells are selected from the group consisting of human hepatoma cell line HepG2(ATCC HB 8065), human liver cell line Chang liver (ATCC CCL 13), murine neuronal cell line C6(ATCC CCL 107), human neuroblastoma cell line BE2 cells (ATCC TIB 182), lymphoma cell line 5F12AD3(ATCC HB 8209) and bovine aortic endothelial cells (BAE).

5. A method for increasing survival rate of cells in animal cell culture under hypoxia condition, which comprises the steps of adding antibiotics of aminoglycosides in a concentration of 10 to 1000 $\mu$g/ml to a culture medium and culturing animal cells without N-type calcium channels.

6. The method for increasing survival rate of cells in animal cell culture under hypoxia condition of claim 5, wherein the aminoglycoside antibiotics are selected from the group consisting of geneticin, neomycin and gentamycin.

* * * * *